United States Patent [19]

Baiocchi et al.

[11] Patent Number: 5,973,150
[45] Date of Patent: Oct. 26, 1999

[54] PHARMACOLOGICALLY ACTIVE ENANTIOMERS

[75] Inventors: Leandro Baiocchi; Valerio Cioli, both of Rome, Italy

[73] Assignee: Angelini Ricerche S.p.A. Societa' Consortile, Rome, Italy

[21] Appl. No.: 09/076,845

[22] Filed: May 13, 1998

Related U.S. Application Data

[62] Division of application No. 08/995,988, Dec. 22, 1997, Pat. No. 5,817,815, which is a division of application No. 08/564,276, Apr. 29, 1996, Pat. No. 5,741,907.
[60] Provisional application No. PCT/EP94/02061, Jun. 21, 1994.

[30] Foreign Application Priority Data

Jul. 1, 1993 [IT] Italy .................. MI93A1418

[51] Int. Cl.$^6$ ................................. C07D 241/04
[52] U.S. Cl. ............................................. 544/384
[58] Field of Search .................... 544/392, 384, 544/395, 406, 408

[56] References Cited

U.S. PATENT DOCUMENTS 3,365,453   1/1968   Archer et al. ........................ 260/268
5,726,178   3/1998   Baiocchi ................... 514/253
5,739,334   4/1998   Baiocchi ................... 544/384
5,741,907   4/1998   Baiocchi et al. ................ 544/366

*Primary Examiner*—Richard L. Raymond
*Assistant Examiner*—Ann Razgunas
*Attorney, Agent, or Firm*—Oblon, Spivak, McClelland, Maier & Neustadt, P.C.

[57] ABSTRACT

(S) or (R) enantiomer of a compound of formula:

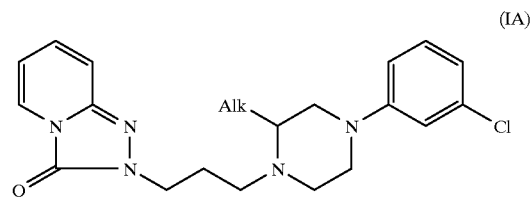

(IA)

where Alk is an alkyl having from 1 to 3 carbon atoms, and an acid addition salt thereof with a physiologically acceptable acid.

1 Claim, No Drawings

PHARMACOLOGICALLY ACTIVE ENANTIOMERS

This application is a Division of application Ser. No. 08/995,988, filed on Dec. 22, 1997, now U.S. Pat. No. 5,817,815, which is a Division of application Ser. No. 08/564,276, filed on Apr. 29, 1996, now U.S. Pat. No. 5,741,907, issued on Apr. 21, 1998, which is the National Stage of International Application No. PCT/EP94/02061, filed Jun. 21, 1994.

DESCRIPTION

This invention relates to pharmacologically active enantiomers, their salts with physiologically acceptable acids, a method for their preparation and the pharmaceutical compositions containing them.

PCT/EP93/00080 describes a class of novel compounds of the general formula:

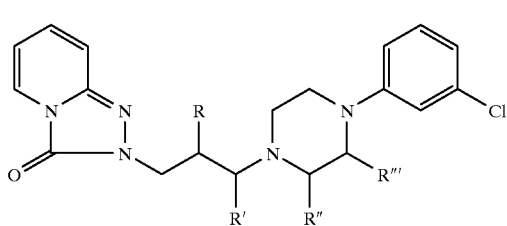

where only one of R, R', R" and R'" is an alkyl having from 1 to 3 carbon atoms while the others are hydrogen.

The pharmacological data reported in the above mentioned application show that the compounds of formula (I) are endowed with a pharmacological profile similar to that of trazodone (I, R=R'=R"=R'"=H) but also have some advantages such as, for example, a reduced affinity for adrenergic receptors.

It has now surprisingly been found that both (S) and (R) enantiomers of the compounds of formula (I), where R, R', R'" are hydrogen and R" is an alkyl having from 1 to 3 carbon atoms, have an improved analgesic activity compared to their racemates.

This finding is even more surprising since both the enantiomers have a lower alphalytic activity, and consequently less undesirable effects, compared to the corresponding racemates.

It is therefore a first object of this invention to provide (S) and (R) enantiomers of the compounds of formula:

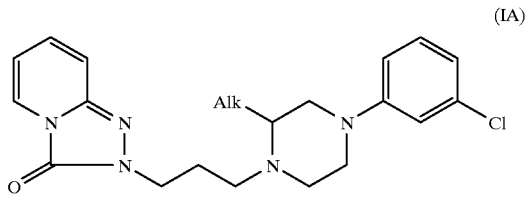

where Alk is an alkyl having from 1 to 3 carbon atoms, and their addition salts with physiologically acceptable acids.

Examples of suitable acids are hydrogen chloride, hydrogen bromide, phosphoric acid, sulfuric acid, lactic acid, succinic acid, acetic acid, tartaric acid, malic acid, citric acid, benzoic acid, 2-naphthalenesulfonic acid, adipic acid and pimelic acid.

Although both (R) and (S) enantiomers are more active than the corresponding racemates, (S) enantiomers are more active than (R) enantiomers. Hence, (S) enantiomers are preferred.

As far as the meanings of Alk are concerned, methyl is preferred.

Thus, the preferred compound of this invention is the (S) enantiomer of formula (IA) wherein Alk is methyl.

The analgesic activity of the compounds of this invention has been proved in mice by means of the phenylquinone test via subcutaneous route (Pharmacol. Exp. Ther., 125, pp 237–240, 1959). Thirty animals were treated with each product. The experimental results are reported in Table 1.

TABLE 1

| Compound IA | | ANALGESIC ACTIVITY |
|---|---|---|
| Form | Alk | Phenylquinone, $ED_{50}$ (mg/kg) |
| Racemate | $CH_3$ | >12.50 |
| (R) | $CH_3$ | 9.02 |
| (S) | $CH_3$ | 7.80 |

Table 1 shows that a higher dose of racemic compound is needed to achieve the same analgesic action. This means that the racemic compound has less analgesic activity compared to the single enantiomers. Table 1 also shows that (S) enantiomer is more active than (R) enantiomer.

Since an interference with the adrenergic system is an index of undesirable effects, both the capability of binding to alpha 1 adrenergic receptors, as $IC_{50}$ (Table 2), and the alphalytic activity (Table 3) of the same compounds have been evaluated. As far as the receptor binding test is concerned, reference is made to "Molecular Pharmacology", 20, 295–301, (1981).

In turn, the aLphalytic activity was evaluated on an isolated organ (deferent of rat) according to the technique described in "Clinical and Experimental Pharmacology & Physiology", 6, 275–279, (1979).

The experimental results are reported in Tables 2 and 3.

TABLE 2

| Compound IA | | Affinity for alpha 1 |
|---|---|---|
| Form | Alk | adrenergic receptors ($IC_{50}$) |
| Racemate | $CH_3$ | 471 |
| (R) | $CH_3$ | 533 |
| (S) | $CH_3$ | 981 |

TABLE 3

| Compound IA | | Alphalytic activity |
|---|---|---|
| Form | Alk | $pA_2$ |
| Racemate | $CH_3$ | 7.70 ± 0.7 |
| (R) | $CH_3$ | 6.75 ± 0.2 |
| (S) | $CH_3$ | 5.40 ± 0.7 |

In Table 2 the affinity for the alpha 1 adrenergic receptors is as much high as low is the value of $IC_{50}$, whereas, in Table 3, the alphalytic activity is as much high as high is the value of $pA_2$. Also the data of Tables 2 and 3 are therefore totally unexpected since they show that both the interference with the adrenergic receptor and the alphalytic activity, and thereby the undesirable effects of both (S) and (R) enantiomers, are lower than those of racemate while the alphalytic activity of (S) enantiomer is lower than that of (R) enantiomer.

Thus, for the enantiomers and the racemate of formula (IA) the greater the analgesic activity the lower the undesired alphalytic activity.

The compounds of this invention can be prepared by fractional crystallization of the salts thereof with an optically active acid, and by stereospecific synthesis.

In the first method the salts with tartaric acid proved to be particularly helpful.

It is therefore a second object of this invention to provide a method for the preparation of enantiomers of formula (IA), characterized in that a racemic compound of formula (IA) is salified with (R,R or S,S) tartaric acid, the pair of the thus obtained diastereoisomeric salts is separated by fractional crystallization from a suitable solvent, and, when desired, the thus obtained enantiomer is salified with a physiologically acceptable acid.

Examples of suitable solvents are lower alcohols and water.

The salts of the enantiomers of this invention with (R,R or S,S) tartaric acid are also novel and therefore are a thir object of this invention.

It is a further object of this invention to provide a method for the stereospecific synthesis of enantiomers of formula (IA) and their addition salts with physiologically acceptable acids, characterized in that a compound of the formula (III):

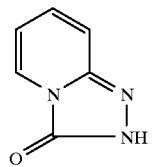

(III)

or an alkali metal salt thereof is reacted with a piperazine compound of formula (II):

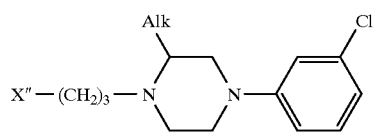

(II)

wherein

Alk has the above mentioned meaning, and X" is a leaving group selected from the group comprising chlorine, bromine and —O—SO$_2$—Z where Z is alkyl or aryl, and Compound (II) has the absolute (R) or (S) configuration, in the presence of a suitable organic diluent or a mixture of organic diluents at a temperature of from 40° C. to the boiling temperature of the reaction mixture, and, when desired, the thus obtained enantiomer is salified with a physiologically acceptable acid.

The above mentioned reaction essentially involves the alkalinization of a secondary amino group and may be carried out according to conventional techniques (J. March, Advanced Organic Chemistry, 3rd ed., J. Wiley & Sons, N.Y., pages 364–365).

Preferably, the compound of formula (III) is reacted in the form of an alkaline salt such as, for example, the sodium salt described by US-A-3.381.009.

Typical meanings of Z are methyl, phenyl, tolyl and p-bromo-phenyl.

The reaction is preferably carried out by reacting the sodium salt of the compound of formula (III) with a compound of formula (II) in the presence of a suitable organic diluent or a mixture of organic diluents at a temperature of from 40° C. to the boiling temperature of the reaction mixture. Examples of suitable organic diluents are: aromatic hydrocarbons, aliphatic alcohols, amides and mixtures thereof.

Examples of preferred aromatic hydrocarbons are benzene, toluene and xylene. Examples of aliphatic alcohols are butanol, t-butanol, s-butanol, isobutanol, pentanol and t-pentanol. A typical example of a preferred amide is dimethylamide.

In turn, the stereospecific synthesis of the compounds of formula (II) can be performed by reacting a compound of formula

(VIII)

where Alk has the above mentioned meaning,
X' is CH$_3$—O—SO$_2$—O— or halogen, and
Y is an alkyl having from 1 to 3 carbon atoms, having the absolute (S) or (R) configuration, with the compound of formula

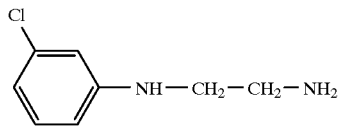

(VII)

to yield a compound of formula

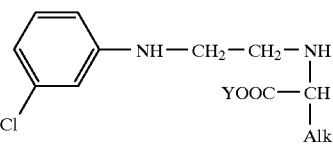

(VI)

where Y and Alk have the above described meaning, having (R) absolute configuration when the Compound VIII has (S) configuration and viceversa.

The reaction between Compound (VIII) and Compound (VII) to yield Compound (VI) is preferably carried out in the presence of an acid acceptor and a suitable solvent.

Examples of suitable acid acceptors are triethylamine and pyridine.

Examples of suitable solvents are the aromatic hydrocarbons such as toluene and xylene.

Compound (VI) is then cyclized to yield a compound of formula

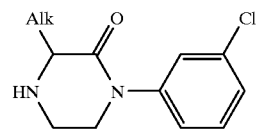

(V)

having the same absolute configuration as Compound (VI).

The cyclization of Compound (VI) to Compound (V) could not be performed with the technique described in PCT/EP93/00080 in connection with the corresponding racemic compounds since said technique caused complete racemization. After a number of unsuccessful attempts which led either to racemization or to recovery of unaltered Compound (VI), it was unexpectedly found that the desired cyclization could be very easily performed by dissolution of Compound (VI) in an aqueous solution of a strong acid and separation, after a brief heating, of the desired Compound (V) by alkalinization of the resultant solution.

A typical example of a preferred strong acid is hydrochloric acid.

Compound (V) thus obtained is then reduced in a manner similar to that described for the reaction Scheme 3 in the above mentioned patent application PCT/EP93/00080.

The prepararation is then prosecuted in a manner similar to that described in the above mentioned patent application in relation to the reaction Scheme 2.

Both during the cyclization step (VI→V) and during all the subsequent steps there is no inversion of the configuration and the thus obtained final compound of formula (IA) has the same absolute configuration as Compound (V). The possibible racemization, if any, is very small.

For practical purposes the compounds of this invention may be administered as they are but it will be preferred to administer them as pharmaceutical compositions.

These compositions are a further object of this invention and contain a therapeutical amount of at least one enantiomer of formula (IA) or of an addition salt thereof with a physiologically acceptable acid, together with liquid or solid pharmaceutical carriers.

The pharmaceutical compositions of this invention may be solid, such as tablets, sugar-coated pills, capsules, powders and controlled release forms, or semi-liquid, such as creams and ointments, or liquid, such as solutions, suspensions and emulsions.

In addition to conventional carriers, the compositions of this invention may contain other suitable pharmaceutical additives, such as preservatives, stabilizers, emulsifiers, salts to regulate osmotic pressure, buffers, colouring and flavouring agents.

If required for a particular therapy, the compositions of this invention may also contain other compatible active ingredients, whose contemporaneous administration is therapeutically useful.

For therapeutical purposes the effective amount of the enantiomer of formula (IA) to be administered can vary widely depending on various factors such as the particular therapy required, the pharmaceutical composition, the method of administration and the effectiveness of the specific enantiomer of this invention that is used. Nevertheless, the optimal effective amount can be chosen by simple routine procedures.

In general, the daily posology of the enantiomers of formula (IA) preferably ranges from 0.1 to 10 mg/kg.

The pharmaceutical compositions of this invention can be prepared according to conventional techniques known to the pharmaceutical chemist, which comprise admixing, granulating and compressing, when necessary, or variously mixing and dissolving the ingredients, when appropriate to obtain the desired result.

The following examples are intended to illustrate this invention without, however, limiting it in any way.

EXAMPLE 1

A mixture of 12.5 g (0.032 moles) of racemate (I, R=R'=R'''=H; R''=CH$_3$), as a base, and 4.8 g (0.032 moles) of naturally occuring (R,R) tartaric acid in 125 ml of absolute ethyl alcohol, was briefly heated at almost boiling temperature until dissolution was complete.

The solid separated by cooling was collected by filtration and recrystallized from absolute ethyl alcohol until a constant melting point was obtained.

m.p. 151–152° C., [alpha]$_D^{20}$=+13.2±0.3 (1% in water).

The corresponding base was obtained by suspension of the salt in water and alkalinization, under stirring, with powdered potassium carbonate.

The residue of the extraction with dichloromethane melts at 63–65° C. (hexane), [alpha]$_D^{20}$=+32.0±0.3 (1% in absolute ethyl alcohol).

Hydrochloride, m.p. 122–124° C. (from ethyl alcohol, hygroscopic);

Sulfate, m.p. 204–205° C.;

Maleate, m.p. 142–143° C.

(R) base was recovered from the filtered solution, from which the (S) (R,R) salt had been previously separated, and was dissolved in absolute ethyl alcohol.

An equimolar amount of (S,S) tartaric acid was then added to this solution. The (R) (S,S) salt was separated by cooling. This salt has the same melting point (151–152° C.) as the (S) (R,R) salt, [alpha]$_D^{20}$=+13.2±0.3.

The corresponding base melts at 63–65° C.; [alpha]$_D^{20}$=−32.0±0.3 (1% in ethyl alcohol).

Hydrochloride, m.p. 122–124° C. (hygroscopic).

EXAMPLE 2 a) (R)-1-(3-chlorophenyl)-3-metyhl-piperazin-2-one (formula V, Alk=CH$_3$)

A solution of 18.4 g (0.108 moles) of N-(3-chlorophenyl)-ethanediamine (J. Med. Chem., 9, 858–860 (1966)), 19.3 ml (0.119 moles) of (S)-methanesulfonyl-lactic acid ethyl ester and 22.8 ml (0.163 moles) of triethylamine in 200 ml of toluene was boiled and refluxed overnight.

The reaction mixture was washed with water and extracted with a solution of 1N hydrochloric acid. The aqueous phase was alkalinized with powdered potassium carbonate and extracted with methylene chloride.

The thus obtained base was purified by flash chromatography (silica gel, hexane-ethyl acetate 1:1).

The oily residue obtained after evaporation of the solvent was dissolved in 10 parts (by weight) of 2N HCl and the resultant solution was boiled until the starting material disappeared (TLC).

The desired product, [alpha]$_D^{20}$=+50.0 was separated by alkalinization with an alkaline carbonate (sodium or potassium).

b) (R)-2-[3-[4-(3-chlorophenyl)-1-(2-methyl)-piperazinyl]-propyl]-1,2,4-triazol[4,3-a]-pyridine-3(2H)-one
(formula IA, Alk CH$_3$)

The title product was prepared, starting from the compound prepared in the previous step (a), in a manner similar to that described in the patent application PCT/EP93/00080.

Base, [alpha]$_D^{20}$=−31.8 (1% in ethyl alcohol).

Hydrochloride, m.p. 122–124° C. (also in admixture with a sample prepared according to Example 1).

The (R)-1-(3-chlorophenyl)-3-methylpiperazine intermediate (formula IV, Alk=CH$_3$) has a rotatory power [alpha]$_D^{20}$=+15.0 (1% in ethyl alcohol).

EXAMPLE 3

(S)-2-[3-[4-(3-chlorophenyl)-1-(2-methyl)-piperazinyl]-propyl]-1,2,4-triazol[4,3-a]-pyridine-3(2H)-one (formula IA, Alk=CH$_3$)

The title product was prepared in a manner similar to that described in Example 2 above except for the substitution of (S)-methanesulfonyl-lactic acid ethyl ester with an equimolar amount of (R)-2-bromo-propionic acid ethyl ester.

Base, m.p. 63–65° C., [alpha]$_D^{20}$=+32.0±0.3 (1% in ethyl alcohol).

We claim:

1. An optically active enantiomer (S) or (R) of formula (V)

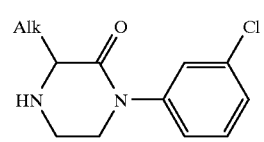

(v)

where Alk is an alkyl having from 1 to 3 carbon atoms.

* * * * *